United States Patent
Groah et al.

(10) Patent No.: US 9,962,416 B2
(45) Date of Patent: May 8, 2018

(54) PROBIOTICS FOR TREATING NEUROPATHIC BLADDER ASSOCIATED URINARY TRACT INFECTION

(71) Applicants: MedStar Health, Columbia, MD (US); Children's National Medical Center, Washington, DC (US)

(72) Inventors: Suzanne L. Groah, Reston, VA (US); Hans G. Pohl, Washington, DC (US); Ljubica Caldovic, Washington, DC (US)

(73) Assignees: Medstar Health, Columbia, MD (US); Children's National Medical Center, Washington, DC (US)

( * ) Notice: Subject to any disclaimer, the term of this patent is extended or adjusted under 35 U.S.C. 154(b) by 0 days. days.

(21) Appl. No.: 14/804,405

(22) Filed: Jul. 21, 2015

(65) Prior Publication Data

US 2016/0015758 A1    Jan. 21, 2016

Related U.S. Application Data

(60) Provisional application No. 62/026,881, filed on Jul. 21, 2014.

(51) Int. Cl.
| | |
|---|---|
| *A01N 63/00* | (2006.01) |
| *A61K 35/747* | (2015.01) |
| *A61K 35/741* | (2015.01) |
| *A61K 9/00* | (2006.01) |
| *A61B 5/20* | (2006.01) |
| *A61B 5/00* | (2006.01) |
| *A61K 35/00* | (2006.01) |

(52) U.S. Cl.
CPC ............ *A61K 35/747* (2013.01); *A61B 5/202* (2013.01); *A61K 9/0034* (2013.01); *A61K 35/741* (2013.01); *A61B 5/4839* (2013.01); *A61K 2035/115* (2013.01)

(58) Field of Classification Search
None
See application file for complete search history.

(56) References Cited

U.S. PATENT DOCUMENTS 5,804,179 A * 9/1998 Bruce .................. A61K 35/747
424/93.45

OTHER PUBLICATIONS

Kontiokari et al. British Medical Journal (2001) 322: 1571-1.*
Hull et al. J. Clinical Microbiol. (1998) 36(1): 115-117.*
Darouiche et al. Urology (2001) 58: 339-344.*
Martins et al. Spinal cord (2013; published online Sep. 12, 2012) 51: 193-195.*
Marelli et al. Eur. Rev. Medical Phrmacol. Sci. (2004) 8: 87-95.*
ATCC webpage for ATCC 53103 lactobacillus Rhamnosus GG https://www.atcc.org/Search_Results.aspx?dsNav=Ntk:PrimarySearch%7c53103%7c3%7c,Ny:True,Ro:0,N:1000552&searchTerms=53103&redir=1 downloaded Aug. 29, 2017.*

* cited by examiner

*Primary Examiner* — Susan M Hanley
(74) *Attorney, Agent, or Firm* — Tarolli, Sundheim, Covell & Tummino LLP

(57) ABSTRACT

A method of diagnosing and selecting treatment for a urinary tract infection (UTI) in a subject having a neuropathic bladder (NB) is described. The method includes screening the subject for UTI risk; selecting a proper lower urinary symptom or UTI treatment if the determined risk exceeds a threshold, wherein the proper treatment is the administration of a therapeutically effective amount of a probiotic treatment to the subject and treating the subject.

8 Claims, 11 Drawing Sheets

PROBIOTICS FOR TREATING NEUROPATHIC BLADDER ASSOCIATED URINARY TRACT INFECTION

CROSS-REFERENCE TO RELATED APPLICATIONS

This application claims priority to U.S. Provisional Application Ser. No. 62/026,881, filed on Jul. 21, 2014, which is hereby incorporated by reference in its entirety.

BACKGROUND

Neuropathic bladder (NB) is defined as a "problem in which a person lacks bladder control due to a brain, spinal cord, or nerve condition." When NB results in incomplete bladder emptying, urinary catheters are often needed. A drawback of catheter use is that bacteria from the gastrointestinal tract and perineum more easily ascend the urethra to the bladder along the surface of the catheter, leading to the nearly universal presence of bacteria in the bladder.

Because catheter-associated urinary tract infection (UTI) is the most common healthcare-associated infection, a tremendous array of resources have been devoted to its prevention, largely centered on curtailing use of, and seeking alternatives to, indwelling urinary catheter use. While these techniques have proven to be effective, there is a large and increasing proportion of the population who require, and benefit from, urinary catheterization due to NB or other medical conditions. These individuals cannot benefit from the prevailing strategies of limiting exposure to urinary catheters.

Clinical dogma has been that "healthy" urine is sterile, and as such the presence of bacteria in the urine (i.e., bacteriuria) not due to sample contamination is considered "abnormal" and perhaps a precursor to UTI. However, it is recognized that under certain conditions, generally associated with poor bladder emptying (i.e., NB), individuals can have bacteriuria and remain asymptomatic (i.e., asymptomatic bacteriuria or ABU). In general, ABU requires no treatment. However, its clinical relevance to the individual with NB, who may not readily perceive symptoms, is poorly understood by most practitioners, leading to uncertainty of whether or not to treat ABU in this population. Further, evidence-based guidelines for UTI diagnosis in people with NB advise against consideration of cloudy, foul-smelling urine or even white blood cells found on urinalysis as indicators of infection. This differs considerably from typical clinical practice, leading to wide variations in diagnostic and prescribing patterns, with widespread overuse of antimicrobials that might disproportionately affect people with NB. Therefore, there is a critical need for novel methods of identifying and treating neuropathic bladder patients with a high risk of UTI.

SUMMARY

Urinary tract infection (UTI) is one of the most common ailments requiring antibiotic therapies as well as prolonged prophylaxis to prevent recurrent infections. Management of UTI for individuals with NB (NB subjects) is problematic due to the difficulty in perceiving urinary symptoms and the presence of nearly constant asymptomatic bacteriuria (ABU). Furthermore, the lack of predictive tools for determining the potential risk of developing symptomatic UTI infections and the development for severe disease and renal scaring can lead to unnecessary antibiotic exposure. Therefore, there is a critical need for novel approaches to screen those individuals with NB with a high UTI risk in order to allow the selection of a proper and timely probiotic treatment. Such methods with allow for the proper management of UTI in individuals with NB while simultaneously promoting antibiotic stewardship.

The inventors hypothesized that the risk of UTI in NB subjects can be determined by monitoring the urinary symptoms of a subject through the administration of a questionnaire and that based on the subject's answers, a proper probiotic treatment can be administered to the subject to effectively manage UTI. It is believed that using the questionnaire is essential to improved urinary symptom and UTI recognition and management in NB subjects.

Using bioinformatic tools, bacteria were isolated from the urine of asymptomatic individuals with NB and compared to normal individuals to identify bacterial traits that are present in subjects with differing risk of UTI. The presence of probiotic species of bacteria in the urine of normal individuals and the presence of bacteria known to be associated with severe urogenital infection in individuals with NB suggests that as opposed to the clinical dogma of bacterial presence in the urine being indicative of disease, a critical component includes the absence of key healthy bacteria found in normal individuals, such as *Lactobacillus*. The absence of key healthy bacteria in the microbiome of individuals with NB further suggests that replenishing the urinary tract microbiome with probiotic bacterium in individuals with NB can be used to effectively prevent and manage lower urinary symptoms and UTI.

BRIEF DESCRIPTION OF THE FIGURES

The accompanying drawings, which are incorporated in and constitute a part of this specification, illustrate some embodiments disclosed herein, and together with the description, serve to explain principles of the disclosed embodiments.

DETAILED DESCRIPTION

Figure 1A:
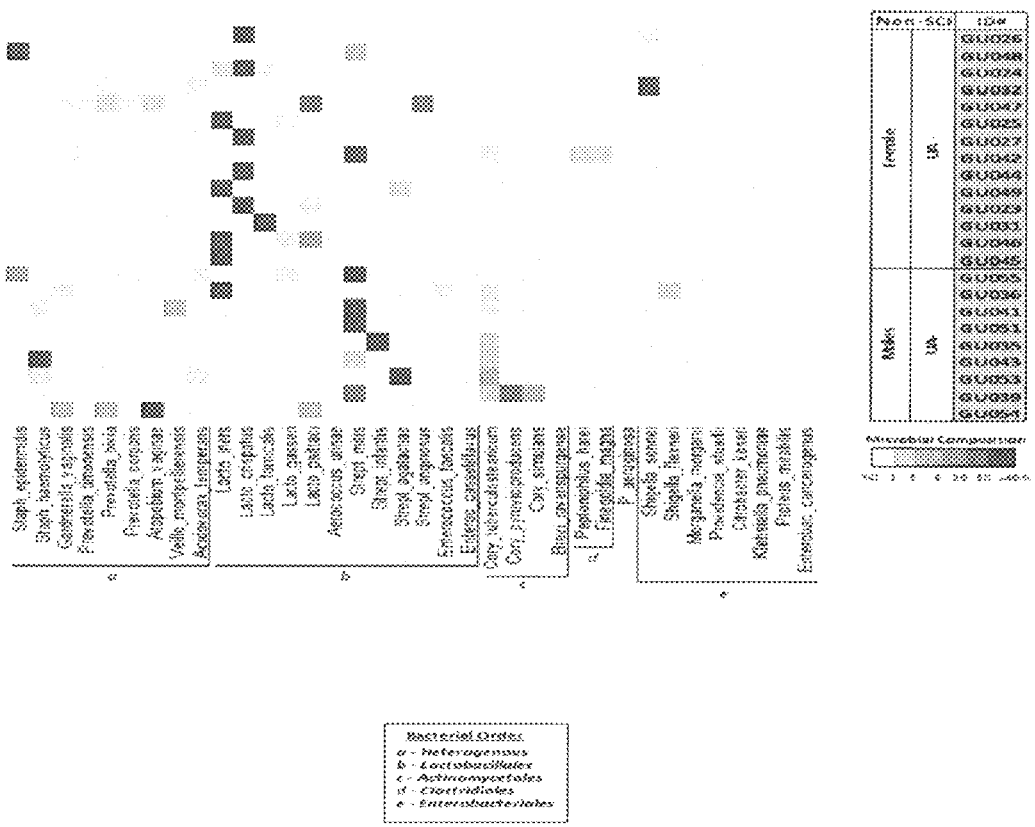
FIG. 1 (A-B) provides graphical illustrations showing heatmaps representing controls (A) and NB subjects (B) where darker shade represents the greatest bacterial counts for individuals including the abundance of *Lactobacillus* species in the control heat map and the relative absence of *Lactobacillus* species in the NB subjects.

A method of diagnosing and selecting treatment for a urinary tract infection (UTI) in a subject having a neuropathic bladder (NB) is described. The method includes screening the subject for UTI risk and selecting a proper UTI treatment if the subject's risk of UTI exceeds a threshold, wherein the proper UTI treatment is the administration of a therapeutically effective amount of a probiotic treatment to the subject.

As used herein, the term "diagnosis" can encompass determining the likelihood that a subject will develop a disease, or the existence or nature of disease in a subject. The term diagnosis, as used herein also encompasses determining the severity and probable outcome of disease or episode of disease or prospect of recovery, which is generally referred to as prognosis). In certain embodiments, the term "diagnosis" includes determining the likelihood that a subject with neuropathic bladder will develop symptomatic urogenital infection, such as a UTI.

As used herein, the terms "treatment," "treating," and the like, refer to obtaining a desired pharmacologic or physiologic effect. The effect may be therapeutic in terms of a partial or complete cure for a disease or an adverse effect attributable to the disease. "Treatment," as used herein, covers any treatment of a disease in a mammal, particularly in a human, and can include inhibiting the disease or condition, i.e., arresting its development; and relieving the disease, i.e., causing regression of the disease. "Treatment," as used herein, covers both prophylactic or preventive treatment (that prevent and/or slow the development of a targeted pathologic condition or disorder) and curative, therapeutic or disease-modifying treatment. In certain embodiments, the term "treatment" can include inhibiting or preventing asymptomatic bacteriuria (ABU) in a subject with neuropathic bladder from progressing to a highly symptomatic urinary tract infection.

As used herein "risk of UTI" can refer to the likelihood or percent possibility of having a urinary tract infection, for example, in comparison with a control subject.

The terms "Probiotic" and "Probiotics" as used herein can be used interchangeably and mean one or more natural, cultured, purified, genetically altered, and/or isolated strains of probiotic bacteria; products of probiotic bacteria; metabolites of probiotic bacteria; and mixtures, blends and combinations thereof that could confer health benefits on the host subject when administered in adequate amounts, more specifically, that beneficially affect a host by improving its urinary system microbial balance, leading to effects on the health or well-being of the host, e.g., a reduction of problematic urinary symptoms related to a urinary tract infection. The probiotics of the present invention can be viable or non-viable when administered and/or when reaching the desired site of administration. The probiotics of the present invention can be administered together as a blend or mixture in a single dosage form, or can be administered in separate dosage forms at separate times.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sample" includes a plurality of such samples.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values; however, inherently contain certain errors necessarily resulting from error found in their respective measurements.

The terms "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. Treatment and evaluation of humans is of particular interest.

Urinary Tract Infection

A urinary tract infection (UTI), as defined herein, is an infection of any part of the urinary tract. The urinary tract includes the kidneys, the bladder, the urethra, and the ureter. Infection of the urinary tract typically results in a variety of symptoms, depending on the specific site of infection. Infection of the kidneys (e.g., acute pyelonepthritis) can result in upper back and side pain, high fever, shaking and chills, nausea, and vomiting. Infection of the bladder (e.g., cystitis) can result in pelvic pressure, lower abdomen discomfort, frequent and painful urination, and blood in the urine. Infection of the urethra (e.g., urethritis) typically includes a burning sensation associated with urination. For febrile UTI, a fever will be present, and possibly other associated symptoms such as shaking and chills as well.

In certain embodiments, the UTI diagnosed and/or treated in accordance with a method of the present invention is a Catheter-Associated Urinary Tract Infection (CAUTI). CAUTI's occur when bacteria or yeast travel along the catheter and cause an infection in a subject's bladder or kidney. The most important risk factor for developing a catheter-associated UTI (CAUTI) is prolonged use of the urinary catheter.

Urinary tract infections can be acute or chronic. An acute UTI is typically short term (i.e., less than one month) and of high intensity, whereas a chronic infection is a longer-term infection (i.e., lasting at least one month, and up to a number of years) that typically does not respond to antimicrobial treatment. In a colonization (i.e., asymptomatic bacteriuria), the patient typically has bacteria growing in their bladder but they do not have symptoms typically associated with a urinary tract infection. An acute infection is present when the patient has symptoms such as painful urination or fever. A fever, as defined herein, is a body temperature above 100.4° F. If an acute infection is present simultaneously with a chronic infection, the effects of the acute infection will dominate those of the chronic infection in terms of overall characterization of the infection, for at least the reason that a chronic infection typically shows few effects.

A urinary tract infection diagnosed in accordance with a method described herein is typically a bacterial infection. The bacteria can be gram-negative bacteria, or the bacterial can be gram-positive bacteria. For example, the bacteria can be one or more of *E. coli, Pseudomonas, Enterococcus, Enterobacter, Klebsiella,* or *Proteus mirabilis*. The majority (80-85%) of bacterial urinary tract infections are caused by *E. coli*. However, a urinary tract infection can also occur as a result of infection by pathogens other than bacteria. For example, urinary tract infections can also be caused by viruses and fungus. Examples of urinary viral infections include those by BK virus, cytomegalovirus (CMV) and Epstein-Barr virus (EBV). Fungal infection is commonly caused by infection by fungi of the genus *Candida*.

In some embodiments, a subject with neuropathic bladder is diagnosed with asymptomatic bacteriuria. In such cases, subjects may not require treatment of any kind and may be further screened for UTI risk as needed in the future. For example, an NB subject screened in accordance with a method described here can have asymptomatic bacteriuria (ABU). ABU is a colonization of a portion of the urinary tract by bacteria that does not display the symptoms typically seen for a urinary tract infection. The urine samples obtained from a subject with asymptomatic bacteriuria may look infected (as evaluated by dipstick, for example) and will result in bacterial growth if cultured. However, it is difficult to determine if this represents an early infection that can be treated briefly to avoid complications, or just bladder colonization with non-pathogenic bacteria that does not represent a problem and will likely not be cleared by treatment with antibiotics. Not all asymptomatic infections represent chronic infections. Some types of subjects will be asymptomatic as a result of a lack of inflammatory response due to immunosuppression (e.g., transplant patients) or lack of sensation of symptoms as a result of, for example, having spinal cord injuries or congenital spinal/neural tube defects.

Subjects with Neuropathic Bladder (NB Subjects)

One aspect of the invention provides a method of diagnosing and selecting treatment of a urinary tract infection (UTI) in a subject having a neuropathic bladder (NB subject). The method includes screening the subject for a UTI risk; selecting a proper UTI treatment if the determined risk exceeds a threshold, wherein the proper UTI treatment is the administration of a therapeutically effective amount of a probiotic treatment to the subject.

In some embodiments, an NB subject can be determined to be a subject who has an increased risk of having a urinary tract infection or is more susceptible to a severe urinary tract infection. A more severe form of UTI can be a UTI exhibiting one or more urinary symptoms that are problematic and/or painful to a subject. An increased risk refers to a higher likelihood or percent possibility of having a urinary tract infection in comparison with a control subject. In some embodiments, a control subject can include an NB subject who is not at an increased risk of UTI (e.g., an NB subject with stable asymptomatic bacteriuria) or a healthy non-NB subject.

Methods described herein can be applied to various subjects in need thereof including individuals, with neuropathic bladder (NB-subjects) who manage their bladders with indwelling catheters. An NB subject's urinary catheter may be used (a) on an intermittent basis for just long enough to empty the bladder, (b) short term (hours or days, e.g. intra- and immediately post-operation), (c) longer term (few days to weeks, e.g. post-operation), or (d) continuous or chronic long term (30 days or more, e.g. spinal cord injuries (SCIs) and in Long Term Care Facilities (LTCFs)). An indwelling catheter that is left in place for a period of time is in general attached to a sterile container to collect the urine. The most commonly used Foley indwelling catheter is a soft silicone or latex tube that is inserted into the bladder through the urethra to drain the urine, and is retained by a small balloon inflated with air or liquid. Urinary catheters come in a large variety of sizes, materials (latex, silicone, uncoated or coated with other materials such as silicone, hydrogel, antibacterial agents, etc.), and types (Foley catheter, straight catheter, Coude-tip catheter, etc.). Catheters are generally placed into the bladder through the urethra, but in some cases, an NB-subject of the present invention may have a suprapubic indwelling catheter that is placed directly into the bladder through a surgically-prepared opening (stoma) in the abdomen above the pubic bone. Catheters can be replaced at a variety of frequencies but are generally replaced about once a month.

While subjects with neuropathic bladder can result from any trauma or disease of the brain or spinal cord, people with spinal cord injury (SCI) and spina bifida (SB) are nearly universally affected. Therefore, in specific embodiments, subjects can include individuals with neuropathic bladder due to spinal cord injury or spina bifida. For example, a subject can include an individual that is 1-year post SCI or a subject at least 6 years old with SB.

Questionnaire

The screening step can be performed using a urinary symptom questionnaire or similar survey instrument. A questionnaire for use in a method described herein can be a tool for an individual to monitor their need to initiate or stop management of lower urinary symptoms through the use of probiotic treatment described below and when to abandon probiotic treatment (e.g., through self-management) in favor of seeking further medical assistance for possible UTI.

In some embodiments, the urinary symptom questionnaire is a subjective urinary symptom questionnaire. The screening step can include having the subject answer questions from a UTI screening questionnaire and scoring the questionnaire. Typically, the questionnaire is performed in private by the subject or a caregiver and the results kept confidential. In some embodiments, methods described herein are performed using a computer process. For example, one or more of the screening, diagnosing, treatment selection, administration steps can be utilized as part of an algorithm implemented in a computer program. The computer program can be run by a health care provider or the subject themselves.

A questionnaire for use in a method of the present invention can include questions related to urinary symptoms, such as those focusing on urinary signs and symptoms of UTI. Questions may refer to the frequency, severity and the impact of urinary symptoms on an individual with neuropathic bladder. A questionnaire for use in a method described herein can be based on patient experiences related to the onset and progression of symptoms that occurred in a previously diagnosed UTI. In some embodiments, additional questions may be added in subsequent questionnaires following administration of a baseline questionnaire.

A questionnaire can include questions in terms of the presence, frequency, severity, and the impact of urinary symptoms on individuals with neuropathic bladder. In some embodiments, the questionnaire can have 200, 150, 100, 50, 30 or fewer items identified as relevant to UTI symptoms in individuals with neuropathic bladder. In some embodiments, the questionnaire can have 15 or fewer items. In some embodiments, subjects are instructed to complete the questionnaire every two weeks. In some embodiments, subjects are instructed to complete the questionnaire once a week. In some embodiments, subjects are instructed to complete the questionnaire whenever urinary symptoms occur to determine whether to initiate probiotic treatment.

Examples of urinary symptoms of UTI to be surveyed in a questionnaire can include but are not limited to dark color urine, blood in urine, pink urine, cloudy and/or milky appearing urine, sediment in urine, white discharge, malodorous urine (bad-smelling, strong, foul, or pungent urine), an increase in bladder spasm, urgency or frequency, incontinence, leakage, ineffective catheterization, pain in abdomen, pain in lower back, pain in legs, pain in penile or urethral region, pain during bladder spasm, burning or irritation on catheterization or passing urine, pain based on body position (sitting versus standing or lying down), feeling feverish, fatigue, lethargy, altered sleep patterns, weakness, irritability, general sense of not feeling well, muscle aches, headaches, dizziness, increased lower body tone, rigor or spasticity, abdominal bloating, nausea, stomach pain, loss of appetite, and changes in bowel patterns.

Scoring of the questionnaire can include providing a cumulative score of the number of items (urinary symptoms) endorsed by the subject or subject caregiver. Scoring can also be related to the frequency, severity and the impact of urinary symptoms on individuals with neuropathic bladder. For example, a subject indicating that they are experiencing greater frequency of a particular urinary symptom may generate a greater relative score.

Based on the answers provided in a questionnaire and/or a generated score, a proper treatment for the NB subject can be selected and/or initiated. For example, probiotic treatment can be initiated when a generated score or set of responses reach a particular threshold of UTI risk. The threshold of UTI risk can be a particular number, amount, degree, and/or a combination of urinary symptoms identified during the screening step (e.g., through the use of a questionnaire) triggering or guiding the selection of the administration of a proper probiotic treatment to the subject but that does not require immediate antibiotic treatment or other relative medical attention. The threshold of UTI risk can be a predetermined number, amount, degree, and/or a combination of urinary symptoms wherein any value greater than the predetermined number, amount, degree, and/or a combination of urinary symptoms triggers or guides the selection of the administration of a proper probiotic treatment to the subject. In some embodiments, the threshold can include a cumulative point total of endorsed items from a questionnaire that is greater than or equal to a point total predetermined by a health care professional that indicates that a subject can benefit from probiotic treatment.

Urinary symptoms identified in a questionnaire and meeting or exceeding a threshold and thus triggering probiotic treatment in an NB subject can be one or more problematic urinary symptoms not commonly found in a control population. In some embodiments, a control population can include individuals with NB having asymptomatic bacteriuria (ABU) that does not proceed to severe urogenital infection. In other embodiments, a control population can include healthy individuals without NB. Therefore, the threshold of UTI risk can be a predetermined number, amount, degree, and/or a combination of urinary symptoms wherein any value greater than the number, amount, degree, and/or a combination of urinary symptoms derived from a control population triggers or guides the selection of the administration of a proper probiotic treatment to the subject.

In some embodiments, no treatment is required or triggered by scoring or reviewing the questionnaire and the subject can continue to be screened using a questionnaire as necessary in the future. In other embodiments, one or more answers to the questionnaire (e.g., that they have a fever greater than 100.4° F.) can indicate that subject requires medical assistance including but not limited to antibiotic treatment. Similarly, if urinary symptoms persist or worsen medical assistance outside of probiotic treatment can be sought but the subject.

Figure 3:
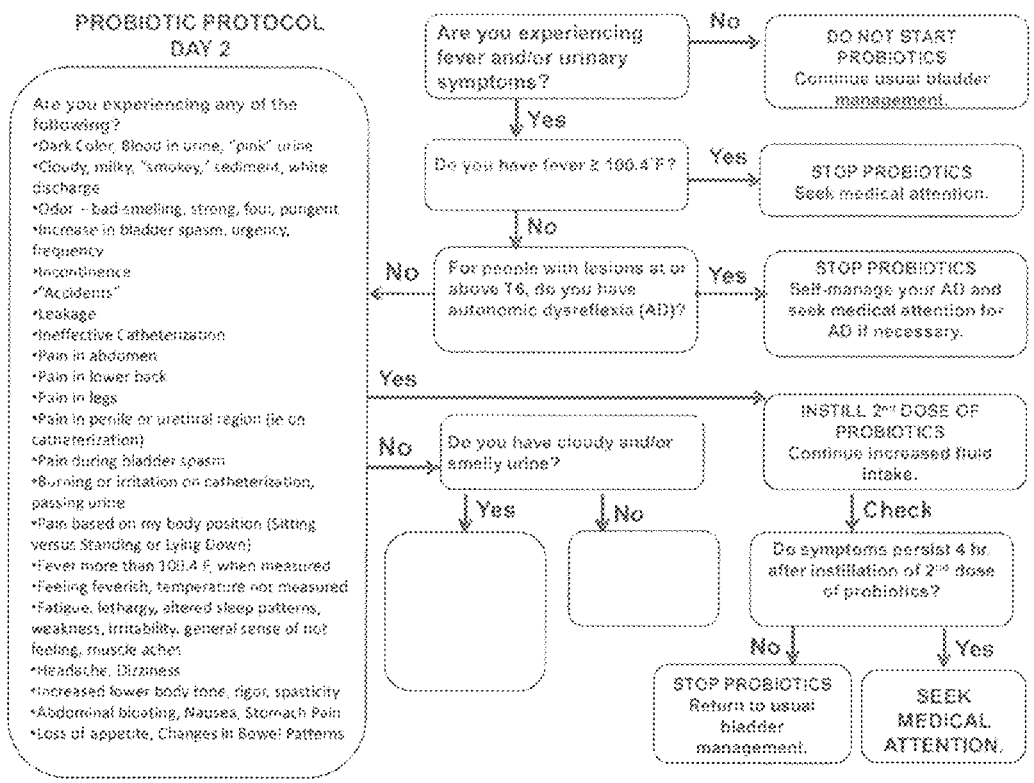
FIG. 3 provides an illustration of a decision tree for a Day 2 probiotic protocol for the identification and treatment of UTI in a subject with neuropathic bladder in accordance with an embodiment of the invention.
Figure 4:
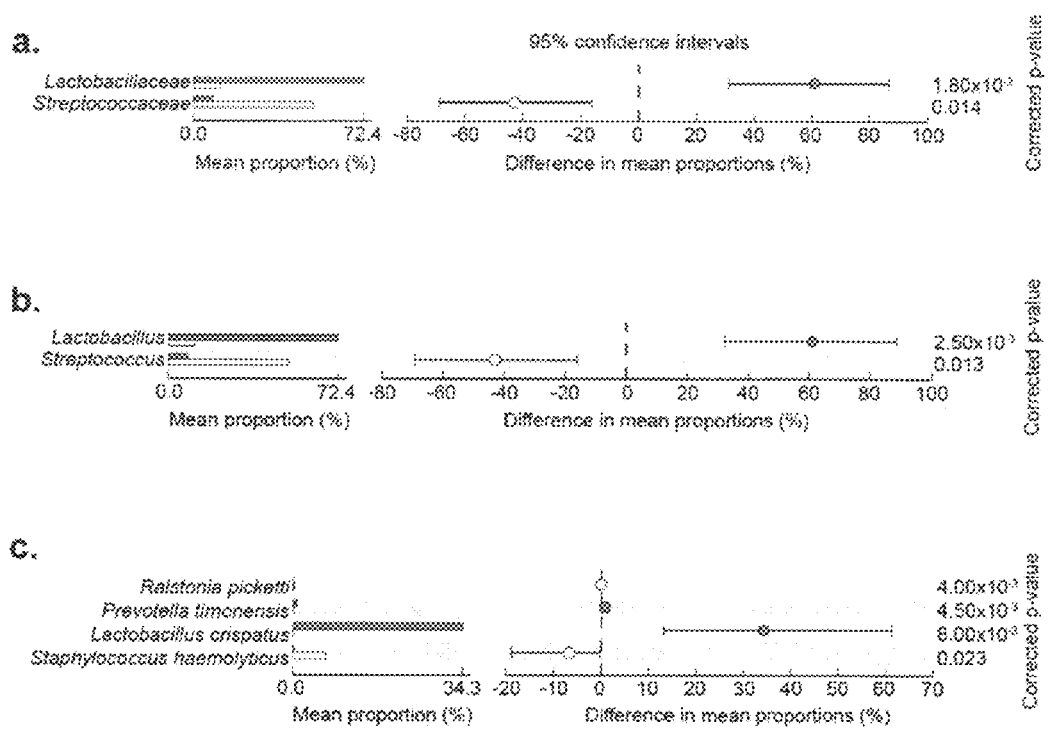
FIG. 4 (A-C) provides graphs showing the significant differences in the urine microbiomes in all females (shaded) vs all males (not shaded) at the (A) family, (B), genus, and (C) species level.
Figure 5:
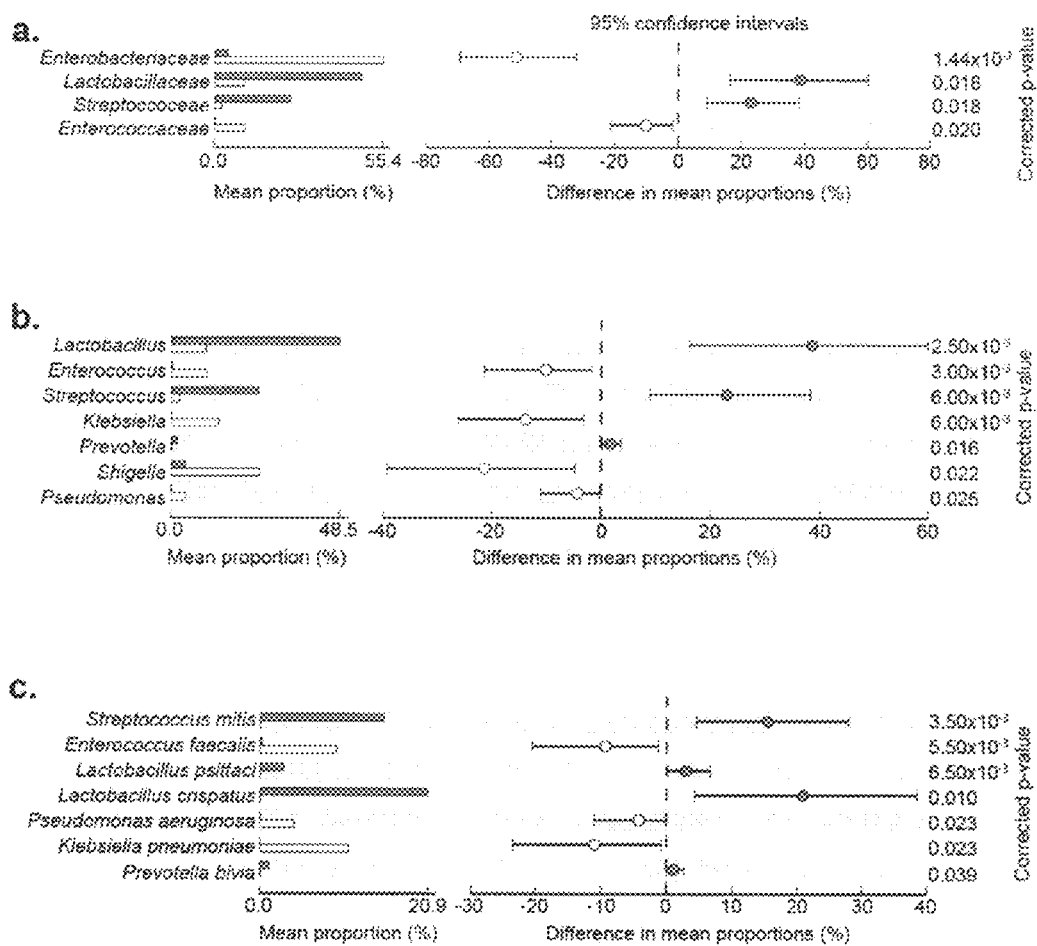
FIG. 5 (A-C) provides graphs showing the significant differences in group urine microbiome analyses of non-NB subjects (shaded) versus NB subjects (not-shaded) at the (A) family, (B), genus, and (C) species level.
Figure 6:
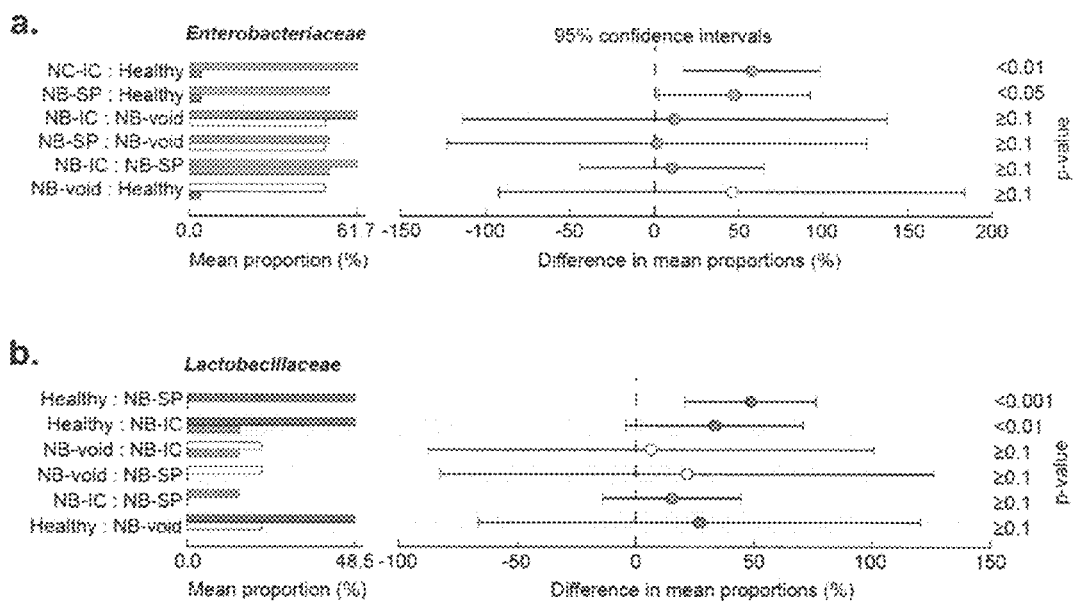
FIG. 6 (A-B) provide graphs showing significant differences in Enterobacteriaceae (A) and Lactobacillaceae (B) by bladder function and bladder management method (shaded=non-NB; no shading=NB subject who void).
Figure 7:
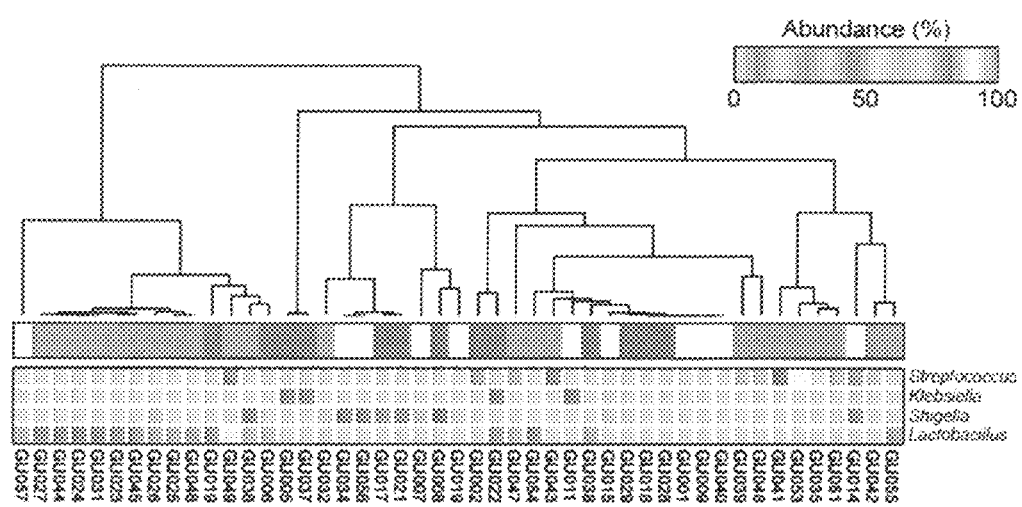
FIG. 7 provides a graphical illustration showing a heatmap and dendrogram of predominant genera by patient group and pyuria status (shaded=NB subjects without pyuria; no shading=NB subject with pyuria).

In some embodiments, the questionnaire is a treatment decision tree embedded in a patient questionnaire. The decision tree can include decision points that guide the selection of proper treatment based on how individuals with neuropathic bladder rate the frequency, severity, or impact of their urinary symptoms, plus any clinical indicators of progression of infection to a point where the individual's risk is inconsistent with continued probiotic treatment and requires medical attention (e.g., where the NB-subject indicates that they have a fever greater than 100.4° F.). An exemplary non-limiting embodiment of a method described herein is shown in FIGS. 3 and 4 where decision trees illustrates a Day 1 and Day 2 probiotic protocol for the screening and treatment of UTI in a subject with neuropathic bladder.

Bacterial Species Associated with Symptomatic UTI in NB Subjects

The step of screening an NB subject for a UTI (e.g., having a urinary tract infection that poses a significant risk of severe and/or problematic urinary symptoms) can further involve detecting or determining the presence of one or more bacterial species associated with urinary tract infections in NB subjects. For example, if during screening the subject exceeds a threshold of urinary symptoms according to the questionnaire, further diagnosis of the subject's UTI can be performed by assaying the subject's urine to determine the presence or absence of bacteria found to be associated with a greater risk of severe urogenital infection.

Therefore, in some aspects of the invention the presence of emerging bacterial species in the microbiome of a subject as determined in a subject's urine sample can be included in a determination to initiate probiotic treatment. In one particular example the presence of *L. biers* and/or absence of *L. crispatus* in an NB subject's urine sample can be indicative of a microbiome at greater risk for disease and can trigger probiotic treatment.

Figure 10:
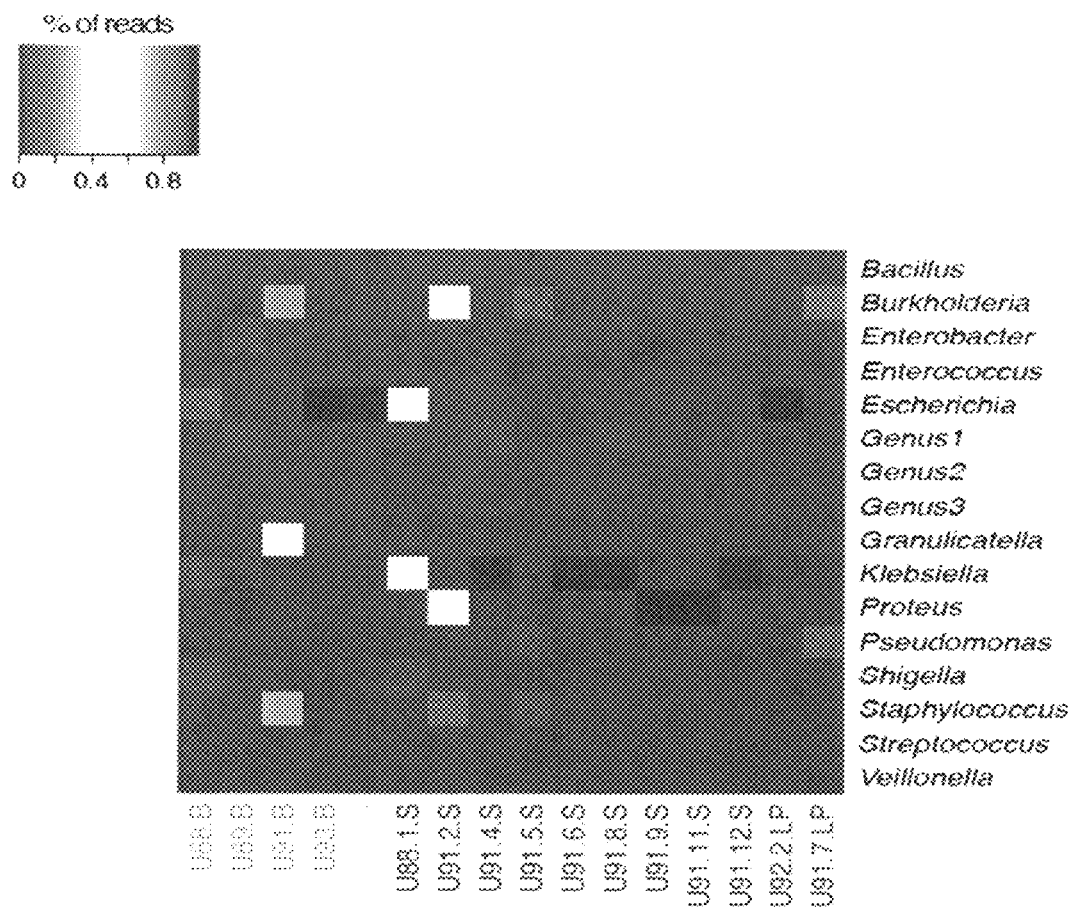

In addition, the presence of *Burkholderia* sp. in urine from a NB subject experiencing repeat UTIs (as shown in FIG. 10) indicates that *Burkholderia* sp. can play a role in repeat UTI infections in NB subjects. Therefore, in some embodiments, a *Burkholderia* sp. in a NB subject's urine can be assayed, wherein the presence of *Burkholderia* sp. can indicate that the subject is at greater risk of severe UTI infection and thus factor into the decision to trigger probiotic treatment as described below.

In some embodiments, any well known UTI screening methods can be used in addition to the methods described herein to confirm or aid in diagnosing UTI infection in a subject. Additional non-limiting screening methods for UTI can include the use of urine culture, blood culture, a complete blood count (CBC), ultrasound, intravenous pyelogram (IVP), and cystoscopy.

Measuring Bacterial Species Levels

In order to determine the bacterial species in a NB subject, a sample including lower urinary system bacteria should be obtained. As the invention is directed towards identifying and treating a subject for a UTI having a significant risk of dangerous or problematic urinary symptoms, the sample should be one including bacterial species associated with UTI. An example of a suitable sample includes urine samples. A variety of methods are known to those skilled in the art for obtaining a urine sample. Urine can be collected from an individual by suprapubic aspiration. This method represents the ideal method for obtaining a urine sample. However, it is not performed routinely in clinical practice in which urine samples are generally obtained after natural micturition; in this setting, some degree of artifactual contamination with normal urethral organisms occurs.

A standard method for obtaining a urine sample can be referred to as the clean-catch sample method. To obtain an untainted urine sample, doctors usually request a so-called midstream, or clean-catch, urine sample. To provide this, the subject washes the area from which urine will issue, urinates a small amount into the toilet for a few seconds and then stops, position the container to catch the middle portion of the stream, urinates until the collection cup is halfway full (about 2 ounces), and then removes the cup. The collection cup should then be sealed with a cap and given to the doctor or sent to the laboratory for analysis.

Alternately, urine can be collected with a catheter. Some patients (small children, elderly people, or hospitalized patients) cannot provide a urine sample. In such cases, a catheter may be inserted into the bladder to collect urine. This is the best method for providing a contaminant-free sample, but has the disadvantage of possibly introducing or spreading infection and discomfort to the subject.

The urine sample may be pretreated as necessary by dilution in an appropriate buffer solution and concentrated or fractionated by any number of methods including but not limited to ultracentrifugation, fractionation by fast performance liquid chromatography (FPLC), or precipitation. Any of a number of standard aqueous buffer solutions at physiological pH, such as phosphate, Tris, or the like, can be used.

Once a sample has been obtained, an analytic device is used to measure the levels of bacterial species. The analytic device can be either a portable or a stationary device. In addition to including equipment used for detecting the bacterial species, the analytic device can also include additional equipment to provide physical separation of analytes prior to analysis. For example, if the analyte detector is an immunoassay, it may also include an ion exchanger column chromatography to purify the proteins from urine before the specific detection of bacterial species by immunoassay. Methods for detecting bacterial species are known to those skilled in the art. For example, urine samples can be assayed using urinalysis, and/or urine culture. An alternate method for determining the predominant bacterial species is by using a polymerase chain reaction (PCR)-based assay, such as multiplex PCR.

In some embodiments, a bacterial species of interest that is shown to be associated with symptomatic urinary tract infections in NB subjects is one that is not routinely cultured. Bacterial species that are not routinely cultured can be assayed using 16S ribosomal sequencing. Unlike capillary sequencing or PCR-based approaches, next-generation-based 16S sequencing (NGS) is a culture-free method that enables analysis of the entire microbial community within a sample. With the ability to combine many samples in a sequencing run, operators can use NGS-based 16S rRNA sequencing as a cost-effective technique to identify strains that may not be found using other methods.

Once the levels of bacterial species have been determined, they can be displayed in a variety of ways. For example, the levels of specific bacterial species can be displayed graphically on a display as numeric values or proportional bars (i.e., a bar graph) or any other display method known to those skilled in the art. The graphic display can provide a visual representation of the amounts of the various bacterial species in the samples being evaluated. In addition, in some embodiments, the analytic device can also be configured to display a comparison of the levels of bacterial species in the subject's urine to a control value based on levels of bacterial species in a comparable urine sample, urine samples from a reference cohort, or a standard numerical reference.

Treatment of Urinary Tract Infection

NB subjects diagnosed or identified as having a high risk of UTI in the screening step as described herein, (e.g., those NB subjects susceptible to severe UTI as determined using a questionnaire described above) can be treated with a proper UTI treatment. A proper UTI treatment selected for a given NB subject can include the administration of a probiotic treatment.

The probiotic(s) used in the methods of the present invention can be any beneficial symbiotic bacteria. The probiotics of the present invention can be viable or non-viable when administered and/or when reaching the desired site of administration. The probiotics of the present invention can be administered together as a blend or mixture in a single dosage form, or can be administered in separate dosage forms at separate times. In addition, when the bacterial strains are taken orally, the bacterial strains must survive the passage through the gastro-intestinal tract and, when the bacterial strains are taken via bladder instillation, the bacterial strains must colonize the lower urinary tract, respectively.

Non-limiting examples of probiotics useful with the present invention include bacteria selected from the group consisting of *Bifidobacterium, Lactobacillus*, and *Streptococcus*. Particular non-limiting examples of probiotics useful herein include *Lactobacillus rhamnosus, Lactobacillus crispatus, Lactobacillus planetarium, Lactobacillus salivarius, Lactobacillus rueteri, Lactobacillus bulgaricus, Lac-* tobacillus casei, Lactobacillus sporogenes, Lactococcus lactis, Biffidophilus infantis, Streptococcus thermophilous, Bifodophilus longum, Bifidobacteria bifidus, Arthrobacter agilis, Arthrobacter citreus, Arthrobacter globiformis, Arthrobacter leuteus, Arthrobacter simplex, Azotobacter chroococcum, Azotobacter paspali, Azospirillum brasiliencise, Azospriliium lipoferum, Bacillus brevis, Bacillus macerans, Bacillus pumilus, Bacillus polymyxa, Bacillus subtilis, Bacteroides lipolyticum, Bacteroides succinogenes, Brevibacterium lipolyticum, Brevibacterium stationis, Kurtha zopfil, Myrothecium verrucaris, Pseudomonas calcis, Pseudomonas dentrificans, Pseudomonas flourescens, Pseudomonas glathei, Phanerochaete chrysosporium, Streptmyces fradiae, Streptomyces cellulosae, Stretpomyces griseoflavus, Bacillus laterosporus, Bacillus bifidum, Bacillus laterosporus, and combinations thereof. In certain embodiments, probiotics for the present invention are non-pathogenic, and/or non-fever-inducing bacteria, such as Lactobacillus bacteria. In some embodiments, probiotic treatment can include administering to the subject bacteria species commonly found in the microbiome of an asymptomatic non-NB subject's urine.

In some embodiments, the probiotic treatment is self administered (or administered with caregiver assistance) and doesn't require a medical professional's presence. In some embodiments, standardized instructions on preparation and administration, including a tutorial on use of the therapeutic probiotics and/or a step by step video can be provided to the NB subject.

In one embodiment, a probiotic treatment can be administered orally, vaginally or rectally, or instilled into the urinary bladder, and preferably including at least one pharmaceutically acceptable carrier. The probiotic can be administered daily, every other day, every two days, or as often or seldom as desired to achieve alleviation of symptoms. The probiotic can be administered in a single unit dose administered at any time during a day. Alternatively the probiotic can be administered in two or more doses administered at a single time of day or at two or more separate times of day.

The probiotic can be incorporated into a unit dosage form. Non-limiting examples of dosage forms of into which the probiotic and any additional material such as a carrier can be incorporated include capsule, chewable tablet, swallowable tablet/pill, buccal tablet, coated tablet, troche, powder, lozenge, soft chew, solution, suspension, spray, extract, tincture, oil, decoction, infusion, syrup, elixir, wafer, food product, and combinations thereof. The dosage forms can comprise ingestable carriers, non-limiting examples of which include solid or liquid filler diluents, encapsulating substances, and mixtures and combinations thereof; sugars; starches; cellulose and its derivatives; powdered tragacanth; malt; gelatin; talc; stearic acid; magnesium stearate; vegetable oils; polyols; agar; alginic acid; pyrogen-free water; isotonic saline; phosphate buffer solutions; wetting agents; lubricants; coloring agents; flavoring agents; preservatives; and combinations thereof.

The therapeutically effective amount of a probiotic treatment administered to a subject as described herein can include an amount of probiotic that is effective to achieve alleviation of symptoms of the health problems, conditions, and/or diseases managed by the methods and of the present invention. The probiotic administered can be administered at a concentration of from about $1 \times 10^3$ to about $1 \times 10^{14}$ colony forming units (cfu) of probiotic, alternatively from about $1 \times 10$ to about $1 \times 10^{14}$ cfu of probiotic, alternatively from about $1 \times 10^7$ to about $1 \times 10^{14}$ cfu of probiotic, alternatively from about $1 \times 10^9$ to about $1 \times 10^{12}$ cfu of probiotic, and alternatively from about $1 \times 10^{10}$ to about $1 \times 10^{12}$ cfu of probiotic, and alternatively from about $1 \times 10^{11}$ to about $1 \times 10^{12}$ cfu of probiotic, per day.

By way of non-limiting example, the administration of a probiotic treatment to a NB subject in need thereof can include intravesicular Lactobacillus instillation where a subject is instructed to mix the contents of a Lactobacillus rhamnosus gg (ATCC 53103) capsule including 10 billion active probiotic cultures of Lactobacillus GG plus Inulin (a prebiotic) into 30 cc sterile 0.9% saline. After mixing, the subject draws up the 30 cc liquid Lactobacillus mixture into a 60 cc catheter tip syringe, instills the mixture via the urinary catheter, and then clamps the catheter for about 30 minutes.

The present invention is illustrated by the following example. It is to be understood that the particular examples, materials, amounts, and procedures are to be interpreted broadly in accordance with the scope and spirit of the invention as set forth herein.

EXAMPLE

Using metagenomics, we have described the urine ecosystem (microbiome) in people with and without NB. Metagenomics allows qualitative, quantitative, and functional examination of the entire microbial complement (including unculturable elements), significantly improving our understanding of microbial behavior during health and disease. In this study, urine was collected from 47 subjects without urinary symptoms (24 controls and 23 subjects with NB). Deep 16S rRNA sequencing of these samples demonstrated that contrary to clinical dogma, healthy urine is not sterile, and urine microbiomes differ according to bladder function.

Figure 1B:
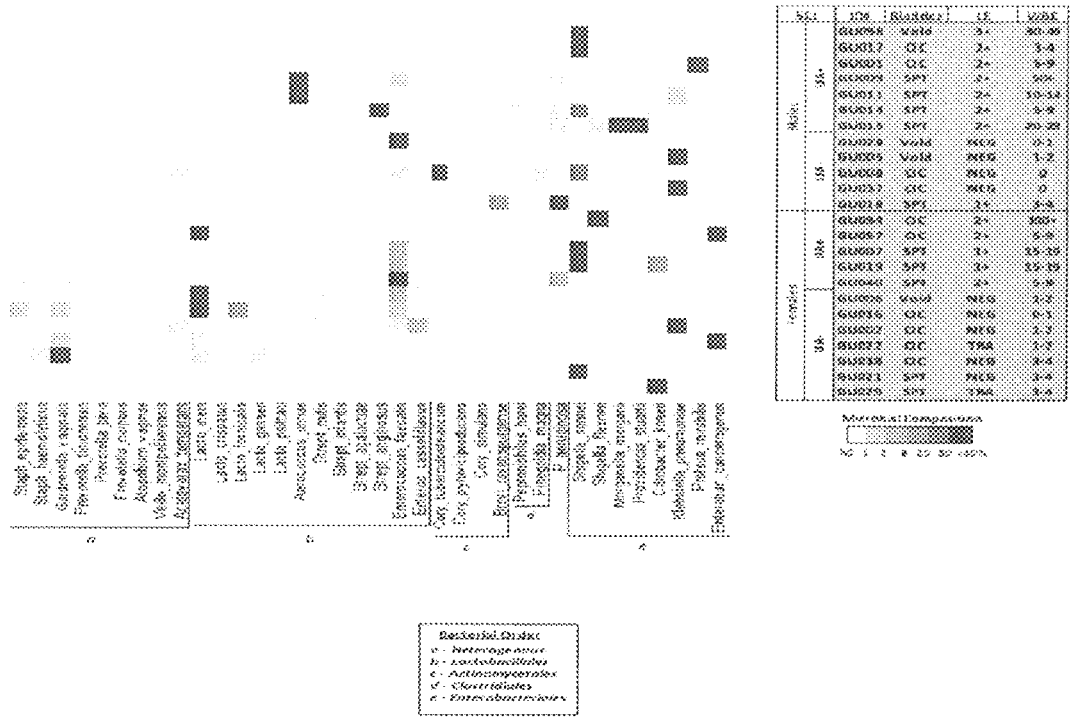

We found that probiotic Lactobacillales species are dominant in control urine samples, while being nearly absent in people with NB. At the same time, pathogenic Enterobacteriales species are prominent in the NB urine samples. The heatmaps below (FIGS. 1A-B) represent controls (1A) and NB subjects (1B), where darker red represents the greatest bacterial counts for individuals (rows). Note the abundance of Lactobacillus species in the upper heatmap (red circle) and relative absence in the lower heatmap (blue circle).

These data suggest that a critical component in UTI development may be an absence of probiotic bacteria, such as Lactobacillus. These pilot data support a bacterial interference model of UTI prevention for people with NB, i.e., encouraging competition between microbial species attempting to colonize and exploit the nutrients of the same environment. Thus, replenishing the microbiome with this probiotic bacterium is anticipated to be clinically beneficial.

B.S. Preliminary Data: Our team is currently in the process of completing the second phase of study using metagenomics to identify changes that occur in the urine ecosystem (also termed the microbiome) in patients with neuropathic bladder. In phase 1, supported by the NIH NCMRR/NINDS 2R24HD050846-06 (NCMRR-DC Core for Molecular and Functional Outcome Measures in Rehabilitation Medicine, P I Hoffinan) and in collaboration with the J. Craig Venter Institute (JCVI), pilot data were collected on 57 subjects without urinary symptoms (25 controls without SCI and 32 subjects with SCI with neuropathic bladder), Deep 16S rRNA sequencing of 57 urine samples was accomplished using amplicon-based 454 Titanium reagents (454 Life Sciences, a Roche company, Branford, Conn., USA). The approach was based on the well validated and successful protocols utilized to process over 1500 samples for the Human Microbiome Project, as well as several thousand other environmental samples. To determine whether distinct microbial signatures were associated with urine cloudiness and white blood cells in the urine (determined by urinalysis samples were grouped by these variables. Taxonomic counts were then normalized by total number of OTUs per sample, and visualized by a heatmap clustering the distribution of OTUs at the level of bacterial genus using the Bray Curtis index. The samples were colored by relative abundance (red/warm most abundant to blue/cool least abundant). Clear urine had a preponderance of Lactobacillus, whereas cloudy urine had a preponderance of Escherichia. Similarly, when data were stratified by 'urine health' {+ or WBC in urinalysis and + or − bacterial load on urine culture), a distinct change in microbial pattern was visualized with the same trend toward a predominance of Lactobacillus in urine samples without WBC versus a lack of Lactobacillus in those specimens of healthy subjects whose urine had WBC and/or bacterial growth on urine cultures. To further differentiate the urine microbiomes of healthy controls and participants with neuropathic bladder, a phylogenic tree was developed (see below). The order Lactobacillales was dominant in control urine samples, while Enterobacteriales were more prominent in SCI urine samples. In the figure below, the right phylogenie tree represents healthy controls and prominence of Lactobacillus is demonstrated by the large green leaf. The phylogenie tree on the left represents the neuropathic bladder group, totally devoid of Lactobacillus. These data demonstrate that contrary to clinical dogma healthy urine is not sterile. Further, microbial signatures in urine differ by amount of WBC in the urine and by cloudiness of the urine. This data suggests that as opposed to our clinical dogma of bacterial presence in the urine being indicative of disease, a critical component may be absence of key healthy bacteria, such as Lactobacillus, suggesting, that replenishing the microbiome with this probiotic bacterium may be beneficial.

A Cross-Sectional Exploratory Metagenomic Study of People at Low- and High-Risk for Urinary Tract Infection The purpose of this work is to supplement available 16S pyrosequencing data from urine samples with PathoScope analysis and compare with traditional clinical assessments to: (1) describe the healthy human microbiome at the species level and (2) determine what subject characteristics are associated with unique urine microbiome(s).

Materials and Methods

This is a cross-sectional study in which asymptomatic volunteers were recruited at a large, urban, rehabilitation facility. Urine samples were obtained from 47 subjects (23 controls without known bladder pathology (non-NB) and 24 subjects with neuropathic bladder (NB) due to spinal cord injury (SCI)). Patient populations, sample collection, urinalysis, isolation of DNA from bacteria, and pyrosequencing of 16S rRNA genes have been described previously. Urinalysis and urine culture values were recorded and for the purposes of this study defined with positive values as follows: leukocyte esterase (LE) ≥1, nitrite (+), pyuria ≥5 white blood cells/high power field (WBC/hpf), presence of cloudy urine (+), and ≥50,000 colony forming 120 units (cfu) bacteria on urine culture.

For PathoScope analysis, NGS alignment and bacterial classification, the raw 16S rDNA data were obtained from the NCBI under BioProject ID 97505. Cutadap and PRIN-SEQ-lite were used to filter out reads of <220 bp, trim primer sequences, and eliminate low-complexity or poor-quality reads. Potential chimeras were also eliminated using UCHIME. 10 Duplicates were retained for downstream analyses. Microbial diversity was characterized in Patho-Scope by mapping reads against two bacterial 16S rRNA data sets (targets), "The All-Species Living Tree" Project LTP115; and a curated version of the Silva 119 (all unclassified and marine microbiome sequences purged). Bowtie2 was used to map reads using settings as implemented in the PathoMap module. An average of 7,541 reads per sample aligned to the target library.

Statistical Analysis

Exploratory analysis and differences in taxon 131 abundances were assessed in R and Bioconductor using packages xlsx, gtools, CHNOSZ, plyr, ggplot2, reshape2, gplots, Phyloseq, and DESeq2, and in STAMP. Alpha diversity indexes of Shannon, Simpson, InvSimpson and Fisher were estimated among groups. Abundance differences among multiple groups of samples were compared using ANOVA and Kruskal-Wallis' tests. If significant ($P<0.05$), the Games-Howell's test was used to determine which means were significantly different between group pairs. Abundance differences between two groups of samples were compared using Welch's test or White's non-parametric t-test. Confidence intervals were estimated by inverting Welch's t-test and using a percentile bootstrapping method (10,000 replications), respectively. False discovery rate (FDR) in multiple testing was controlled by using the Benjamin-Hochberg FDR or Storey's FDR methods.

Results

Urinalysis and urine culture: Bladder management, urinalysis, and urine culture data are shown in Table 1. When urine sample characteristics of 23 non-NB subjects (mean age 35.3 years) and 24 NB subjects (mean age 40.3 years) were compared, the NB group were significantly more likely to have urinalyses positive for LE ($p<0.001$), nitrite ($p<0.001$), pyuria ($p=0.001$), cloudy urine ($p<0.001$), and positive culture ($p<0.001$).

|  | Age (years, range) | Urinalysis | | | | Urine Culture Positive |
|---|---|---|---|---|---|---|
|  |  | +LeukEst (%) | +Nitrite (%) | +Pyuria (WBC > 5/hpf) (%) | Urine Cloudy (%) | (>50,000-100,000 CFU/ml) (%) |
| Non-NB (N = 23) | 35.3 (22-57) | 2 (8.69%) | 0 | 1 (4.35%) | 0 | 3 (13.04%) |
| Males (N = 9) | 34.4 (24-50) | 1 (11.11%) | 0 | 0 | 0 | 0 |
| Females (N = 14) | 35.8 (22-57) | 1 (7.14%) | 0 | 1 (7.14%) | 0 | 3 (21.42%) |
| NB (N = 24) | 40.33 (19-61) | 13 (54.17%) | 11 (45.80%) | 11 (45.80%) | 19 (79.10%) | 17 (70.80%) |

-continued

|  | Age (years, range) | Urinalysis | | | | Urine Culture Positive (>50,000-100,000 CFU/ml) (%) |
|---|---|---|---|---|---|---|
|  |  | +LeukEst (%) | +Nitrite (%) | +Pyuria (WBC > 5/hpf) (%) | Urine Cloudy (%) |  |
| Males (N = 12) | 32.8 (19-48) | 8 (66.66%) | 6 (50%) | 6 (50%) | 11 (91.66%) | 10 (83.33%) |
| Void (N = 3) | 32.6 (19-48) | 1 (33.33%) | 1 (33.33%) | 1 (33.33%) | 2 (66.66%) | 3 (100%) |
| IC (N = 4) | 39.25 (21-48) | 2 (50%) | 3 (75%) | 1 (25%) | 4 (100%) | 3 (75%) |
| SP (N = 5) | 27.8 (20-48) | 5 (100%) | 2 (40%) | 4 (80%) | 5 (100%) | 4 (80%) |
| Females (N = 12) | 47.8 (36-61) | 5 (41.66%) | 5 (41.66%) | 5 (41.66%) | 8 (66.66%) | 7 (58.33%) |
| Void (N = 1) | 41.0 | 0 | 0 | 0 | 0 | 1 (100%) |
| IC (N = 6) | 50.8 (36-55) | 2 (33.33%) | 2 (33.33%) | 2 (33.33%) | 4 (66.66%) | 2 (33.33%) |
| SP (N = 5) | 45.6 (40-61) | 3 (60%) | 3 (60%) | 3 (60%) | 4 (80%) | 4 (80%) |

Microbiome: All subjects (47/47) had bacteriuria based on 16S pyrosequencing, while only 23 of these had positive urine cultures. Among the 23 positive urine cultures, *Escherichia coli* was the most frequently identified species, identified in nine by standard cultivation methods, four of which as the single species, and in the remainder as part of a polymicrobial culture (see Table 2). One culture-positive *E. coli* sample was not confirmed by sequence analysis by either database (although PathoScope detected *Shigella*, which has a nearly identical 16S gene). In two additional cases, bacteria (*Enterococcus faecalis* and *Pseudomonas aeruginosa*) were identified by cultivation, as part of polymicrobial cultures, whose presence could not be confirmed by sequence analysis (although PathoScope detected other species from the same genera). Overall, there was high correlation in the bacterial species identified by both databases with the exception of *E. coli*. None of the *E. coli* strains were identified using the LTP115 database, while 8 of 9 *E. coli* culture positive samples were confirmed to have *E. coli* rRNA using the Silva database. This difference between the two databases is attributable to the LTP115 database including only one *E. coli* reference, while the curated SILVA database includes 1256 *E. coli* (some redundant) references. These results also confirm 164 the good performance of PathoScope at assessing bacterial composition using 16S sequences.

TABLE 2

Comparison of Urine Culture and Sequencing Findings (using two databases)

|  | Patient | Culture | LTP115 | silva119refNRclean |
|---|---|---|---|---|
| *E. coli* as sole organism | GU008 | *Escherichia coli* | − | + |
|  | GU021 | *Escherichia coli* | − | + |
|  | GU026 | *Escherichia coli* | − | − |
|  | GU032 | *Escherichia coli* | − | + |
|  | GU034 | *Escherichia coli* | − | + |
| *E. coli* as part of polymicrobial culture | GU014 | *Enterococcus faecalis* | + | − |
|  |  | *Escherichia coli* | − | + |
|  |  | *Pseudamonas aeruginosa* | + | + |
|  | GU015 | *Enterococcus faecalis* | + | + |
|  |  | *Escherichia coli* | − | + |
|  |  | *Klebsiella pneumoniae* | + | − |
|  |  | *Providencia stuartii* | + | + |
|  |  | *Pseudomonas aeruginosa* | + | + |
|  | GU029 | *Citrobacter koseri (diversus)* | + | + |
|  |  | *Enterococcus faecalis* | − | − |
|  |  | *Escherichia coli* | − | + |
|  | GU056 | *Enterococcus faecalis* | + | − |
|  |  | *Escherichia coli* | − | + |
| non *E. coli* bacteria as monobacterial culture | GU001 | *Proteus* | + | + |
|  | GU005 | *Klebsiella pneumoniae* | + | + |
|  | GU037 | *Klebsiella pneumoniae* | + | + |
|  | GU057 | *Klebsiella oxytoca* | − | + |
|  | GU006 | *Enterococcus faecalis* | + | + |
|  | GU028 | *Enterococcus faecalis* | + | + |
|  | GU018 | *Pseudomonas aeruginosa* | + | + |
|  | GU025 | *Staphylococcus* | + | + |

TABLE 2-continued

Comparison of Urine Culture and Sequencing Findings (using two databases)

| | Patient | Culture | LTP115 | silva119refNRclean |
|---|---|---|---|---|
| | GU046 | *Lactobacillus* species | + | + |
| | GU047 | *Lactobacillus* species | + | + |
| | GU049 | *Streptococcus* beta-hemolytic | + | + |
| | GU053 | *Streptococcus* beta-hemolytic | + | + |
| Samples with non *E. coli* bacteria as polymicrobial culture | | Diphtheroids (*Corynebacterium*) | + | − |
| | | *Lactobacillus* species | + | + |
| | | *Pseudomonas aeruginosa* | − | − |
| | | *Enterococcus faecalis* | + | + |
| | | *Pseudomonas aeruginosa* | + | − |

The non-NB female urine microbiome was characterized by Lactobacillaceae, Aerocacaeae, and Enterobacteriacea, with only Lactobacillaceae being significantly more abundant when compared with non-NB males (75% greater abundance, p=0.002), NB males (60% greater abundance, p=0.01), and NB females (55% greater abundance, p=0.02). There was no gender difference in proportional representation of Lactobacillaceae within the NB group (p>0.1). The non-NB female *Lactobacillus* community was characterized by *L. crispatus* and *L. iners*, whereas the *Lactobacillus* community of NB females was characterized by *L. iners*. *L. crispatus* was not identified in the microbiome of any subject with NB.

Figure 8:
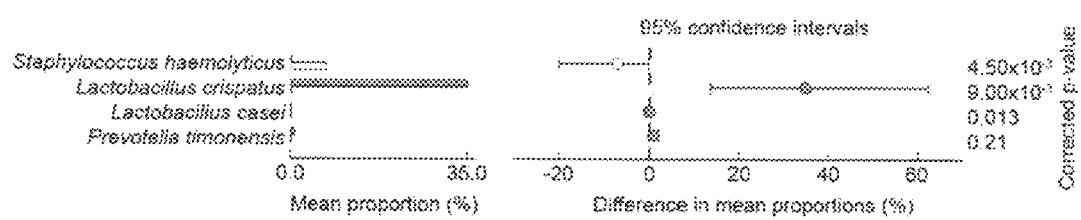
FIG. 8 provides a graph showing confirmation of significant differences in the urine microbiomes of all females (shaded) versus all males (not shaded) at the species level using the SILVA database.

The non-NB male urine microbiome was characterized by a significantly greater proportion of Streptococcaceae than non-NB females (40-45% greater abundance, p=0.014) (FIG. 1a), and NB males and females (both p<0.05). These trends were similar at the genus level (FIG. 1b), but did not persist to the species level. *Staphylococcus haemolyticus* was the one bacterial species present to a significantly greater degree when compared with non-NB females (p=0.023) (see FIG. 1c). FIG. 8 confirms these differences using the SILVA reference database.

Figure 2:
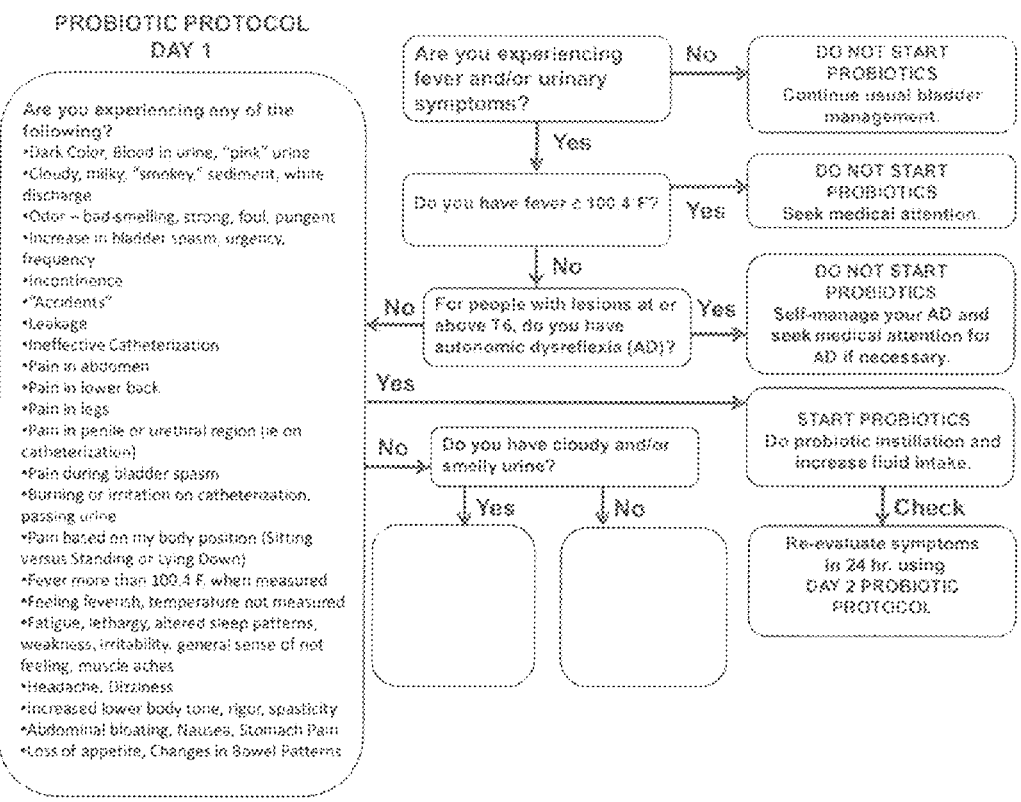
FIG. 2 provides an illustration of a decision tree for a Day 1 probiotic protocol for the identification and treatment of UTI in a subject with neuropathic bladder in accordance with an embodiment of the invention.
Figure 9:
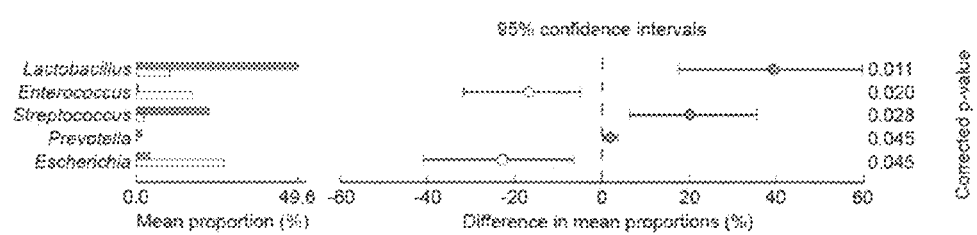
FIG. 9 provides a graph showing significant differences in group urine microbiome analyses of non-NB subjects (shaded) versus NB subjects (not shaded) at the genus and species levels FIG. 10 provides a graphical illustration showing a heatmap of bacterial genus by NB subject (measured using 16S sequencing) and state of health from urine samples taken from 8 adult SCI pateints. *Klebsiella*, *Proteus*, and *Burkholderia* are shown to be related to the presence of symptoms. *Burkholderia* species were found in high abundance during symptomatic state only and after treatment with antibiotics in one patient.
Figure 9:
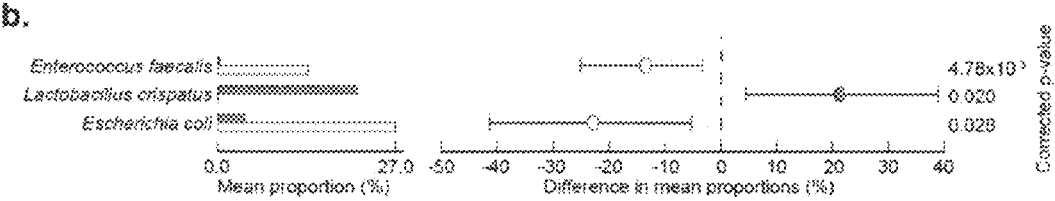

At the genus level, NB females had a significantly greater proportion 183 of *Lactobacillus* (20% greater, p=0.018), *Gardnerella* (8% greater, p=0.02), and *Enterobacter* (6% greater, p=0.04) than NB males. At the species level, *G. vaginalis* (8% greater, p=0.009) and *L. iners* (17% greater, p=0.01) were significantly more predominant in NB females. To determine urine microbiome differences by bladder function, non-NB males and females were combined and compared with NB males and females. FIG. 2c shows that NB group microbiomes had significantly greater representation from *Enterococcus faecalis* (p=0.006), *Pseudomonas aeruginosa* (p=0.023) and *Klebsiella pneumonia* (p=0.023). The greater proportion of *L. crispatus* in the non-NB group persisted in group bladder function analysis (p=0.01). Using the SILVA reference database, significant abundance of *E. faecalis* (p=0.005) and *L. crispatus* (p=0.02) were confirmed for the NB and non-NB groups, respectively, while *E. coli* was also shown to be present in the NB group to a greater extent (p=0.028, see FIG. 9)

When the NB group was further stratified by catheterization status, NB subjects using suprapubic catheters (SP; p<0.05) and intermittent catheterization (IC; p<0.01), but not those with NB who void (p≥0.1) had significantly greater abundance of the family Enterobacteriaceae than the non-NB group (see FIG. 3a). No differences were observed in intra-NB group comparisons. The non-NB group had significantly greater proportions of Lactobacillaceae than subjects with NB using SP catheters (p<0.001) and IC (p<0.01), but not those with NB who void (p>0.1; see FIG. 3b).

Microbial diversity was assessed using the Shannon, Simpson, Inverse Simpson and Fisher diversity indices. While there was no significant difference in diversity between the non-NB, NB206 void, NB-IC, or NB-SP groups, the NB-void group trended toward less diversity. Similarly, there was no difference in diversity by gender between the non-NB and NB groups. All study groups independent of gender and bladder status had a median of two to 18 phylotypes, underscoring the concept that polymicrobial urine is a ubiquitous condition.

When the relationship between microbial diversity and pyuria was assessed, there was no difference in diversity between the NB group in those with and without pyuria. Further analysis by white blood cell (WBC) count demonstrated no association (positive or negative) between the presence of *Lactobacillus* (*L. iners, L. crispatus, L. fornicalis*, and *L. gasseri*), *Streptococcus, Klebsiella*, or *Shigella* and pyuria between the non-NB and NB groups and within the NB group when data were analyzed using both the LTP115 (see FIG. 4) or SILVA reference databases.

When we analyzed the microbiomes of NB subjects by the presence or absence of pyuria we found that the Genus *Actinobaculum* was strongly associated with the presence of pyuria (p=0.009). Further analysis of this genus revealed that none of the four *Actinobaculum* species were present in any non-NB subject or NB subjects with WBC<5, while *Actinobaculum* sp. (*A. schaalii* and *A. massiliense*) were present in 36% (4 of 11) NB subjects with pyuria.

Discussion

Here we aimed to build upon our previous work disputing clinical dogma that healthy urine is sterile, by describing unique asymptomatic urine microbiomes by gender in those with normal and neuropathic bladders. We extend our prior work by correlating clinical status (urinalysis and urine culture) with the urine microbiome, and demonstrating that the asymptomatic urine microbiome varies by gender, with *Lactobacillus* sp. and *S. haemolyticus* characterizing non-NB females and males, respectively. The 'healthy' NB urine microbiome is characterized by known uropathogens, *E. coli, E. faecalis, P. aeruginosa* and *K. pneumoniae*. Lastly, we identified the presence of emerging uropathogens of the genus *Actinobaculum* in healthy NB subjects, all of whom had pyuria.

Our demonstration of the discordance between urinalysis findings and urine culture bacterial growth between the non-NB and NB groups support clinical observations. Further, while sample sizes were small when groups were stratified, there was the suggestion of increasingly abnormal findings with increased exposure to a urinary catheter. Because these patients were asymptomatic, these findings loosely support disregard of WBC (at least at the WBC≥5 level) for catheter-associated UTI diagnosis endorsed by the Infectious Diseases Society of America (IDSA).

Our findings of significant differences in urine microbiome composition by gender, regardless of NB or catheterization status, are not surprising. The normal vaginal microbiome is rich in Lactobacilli during health, and characterized by a loss of Lactobacilli with overgrowth and heightened bacterial diversity during disease states. Related to our findings, *L. crispatus* vaginal microbiomes are considered the 'healthiest' and less likely to be associated with disease states than *L. iners* vaginal microbiomes. If the urine microbiome follows vaginal microbiome physiology then this finding leads us to hypothesize that absence of *L. crispatus* in favor of *L. iners* in NB subjects may be indicative of a microbiome more prone to disease.

The preponderance of Enterococcaceae in the urine microbiome of people with NB is consistent with clinical observations. The NB participants in this study were all affected by spinal cord impairment, which results in near universal presence of neuropathic bladder and bowel. Fecal incontinence or bowel care regimes may alter colonization of the perineum by fecal flora. Alternatively, shifts in the gut microbiome may influence the ability of specific bacteria to colonize the urinary tract independent of mechanical delivery.

Lastly, we were surprised that we did not find any differences in diversity amongst the groups. The evidence suggests that microbiome diversity is not consistently associated with health or disease across body systems. Whereas increased bacterial diversity is associated with disease states in the female vagina, decreased gut microbiome diversity is implicated in obesity and allergic/immunologic conditions. Our data provide preliminary evidence about diversity of the urinary microbiome during the asymptomatic state.

These findings are highly clinically relevant to the NB population, who face a disproportionately high risk of genitourinary complications. UTIs were historically the most common cause of death for people with SCI, and while early mortality due to UTI and subsequent kidney failure has declined with improved prevention and management, UTIs remain the most common cause of emergency department visits and rehospitalization among people with neuropathic bladder.

Our results demonstrate that the Genus *Actinobaculum*, comprised of *A. massiliense, A. schaalii, A. suis* and *A. urinale*, was strongly associated with the presence of pyuria. Characterized by 16S rRNA sequencing between 1997 (*A. schaalii*) and 2003 (*A. urinale*), the four *Actinobaculum* species have been identified as emerging uropathogens in adults and children with underlying pathophysiology, such as: pyelonephritis in a child with ureteropelvic junction obstruction; in a child with neuropathic bladder due to meningomyelocele; chronic renal failure; urosepsis; UTI in the elderly population with chronic cystitis; endocarditis; and Fourniers gangrene. In a study of 10 Danish patients infected with *A. schaalii*, 3 of these were similar to our NB population in that they either utilized a urinary catheter for bladder drainage and/or had neuropathic bladder due to syringomyelia or chronic paraplegia.

*A. schaalii* is a facultative anaerobic gram-positive rod that resembles normal skin or mucosal flora. It is slowly growing and is often overgrown in culture media by faster growing or commensal species. Because of these features and because traditional urine samples are incubated for 24-48 hours in ambient air, *A. schaalii* growth is impeded, making it challenging to isolate. In a retrospective series of 20 cases of *A. schaalii* infection, leukocytes were present in all culture positive cases (10/10) while nitrite was negative in all cases. *A. schaalii* has diminished sensitivity to first line antibiotics used to treat readily cultured uropathogens (i.e. ciprofloxacin and trimethoprim/sulfamethoxazole), while being susceptible to amoxicillin ceftriaxone, gentamicin, and nitrofurantoin. This is clinically relevant as people with NB due to spinal cord injury frequently have pyuria and bacterial growth on urine cultures despite a lack of symptoms. Also, they frequently experience "recurrent" infections that do not respond as well as anticipated to antimicrobials. Thus, we speculate that in people with NB due to spinal injury, the presence of *Actinobaculum* may influence abnormal urinary findings and that standard urine culture data might sometimes mislead antibiotic choice.

The major limitation of this study was the small sample size, which limited the robustness of analyses when multiple stratifications were performed. While we found unique microbiomes by gender and bladder function, our sample was not large enough to stratify by both variables simultaneously. Our ability to identify *E. coli* using 16S rRNA gene sequencing depended on the reference database used. Because this was a cross-sectional study of the urine microbiome during the healthy state, we are unable to make any correlations to UTI or to fluctuations in the microbiome over time. Despite these limitations, given that all 47 patients had bacterial 16s rRNA detected we suspect that bacteria are always present in the urine. Prospective studies of people during asymptomatic, symptomatic and post-antimicrobial therapy will be helpful in better understanding any relationships between these states.

CONCLUSIONS

Several findings from this study suggest a change in our clinical and research approaches to asymptomatic bacteriuria and potentially UTI. Asymptomatic bacteriuria is often considered an 'unhealthy' state or possibly a precursor to disease. Our data suggest that rather than asymptomatic bacteriuria being a rare and episodic event, it is universal across gender and bladder status. Metagenomics allows greater specificity and perhaps will allow us to identify urine microbes that are associated with more or less healthy urologic states, as has been done in other body systems. While our results suggest that jettisoning of the term "asymptomatic bacteriuria" may be premature at this time, with emerging technology enhancing our ability to identify and understand the clearly present urine microbiome, this term will likely become passé. Defining the healthy urine microbiome provides yet undiscovered insights into novel diagnostic and therapeutic approaches worthy of future scientific pursuit. Our findings call into question our current approach to cultivation and perhaps the diagnostic utility of identifying the most prevalent bacterial species as the etiology of infection. Instead of a goal being eradication of bacterial load, perhaps future goals might involve manipulation of the urine microbiome toward a healthier state. For example, *L. crispatus*, which we found in non-NB females, is currently being explored as a probiotic in clinical trials. Different microbiomes (such as those of the gut, vagina, and bladder), and changes within these microbiomes, may be found to influence each other such that deviations toward or away from health in one may affect the others. Understanding the behavior of bacteria within and between microbiomes offers great potential for clinical advancement and benefit to the patient.

What is claimed is:

1. A method of diagnosing and selecting treatment for a urinary tract infection (UTI) in a subject having a neuropathic bladder (NB), comprising:
   screening the subject for UTI risk;
   selecting a proper lower urinary symptom treatment or UTI treatment if the subject's risk of UTI exceeds a threshold, wherein the proper treatment is the administration of a therapeutically effective amount of a probiotic treatment to the subject, wherein the probiotic treatment includes intravesicularly administering to the subject *Lactobacillus rhamnosus* GG; and
   administering the proper lower urinary symptom treatment or UTI treatment to the subject.

2. The method of claim 1, wherein the step of screening the subject for UTI risk comprises providing a questionnaire to the subject, wherein the subject completes the questionnaire, and determining the UTI risk of the patient based on the data from the questionnaire.

3. The method of claim 2, wherein the questionnaire comprises questions related to frequency, degree of severity and/or impact of urinary symptoms on the subject.

4. The method of claim 1, wherein the probiotic treatment is self-administered to the subject.

5. The method of claim 4, further comprising providing to the subject preparation instructions for the probiotic treatment.

6. The method of claim 1, wherein the UTI is a Catheter-Associated Urinary Tract Infection (CAUTI).

7. The method of claim 1, wherein the UTI is a non-febrile UTI.

8. The method of claim 1, the therapeutically effective amount comprising the amount the required to reduce the frequency, degree of severity and/or impact of urinary symptoms on the subject.

* * * * *